US009579171B2

United States Patent
Lorünser et al.

(10) Patent No.: US 9,579,171 B2
(45) Date of Patent: Feb. 28, 2017

(54) PROCESS FOR MANUFACTURING A DENTAL RESTORATION PART AND A DENTAL FURNACE FOR MANUFACTURING THE SAME

(71) Applicant: Ivoclar Vivadent AG, Schaan (LI)

(72) Inventors: Johannes Lorünser, Bludenz (AT);
Michael Brotzge, Koblach (AT);
Robert Grünenfelder, Eschen (LI);
Philipp Kettner, Rankweil (AT)

(73) Assignee: Ivoclar Vivadent AG, Schaan (LI)

( * ) Notice: Subject to any disclaimer, the term of this patent is extended or adjusted under 35 U.S.C. 154(b) by 107 days.

(21) Appl. No.: 14/367,962

(22) PCT Filed: Oct. 24, 2013

(86) PCT No.: PCT/EP2013/072287
§ 371 (c)(1),
(2) Date: Jun. 23, 2014

(87) PCT Pub. No.: WO2014/095134
PCT Pub. Date: Jun. 26, 2014

(65) Prior Publication Data
US 2015/0238288 A1    Aug. 27, 2015

(30) Foreign Application Priority Data

Dec. 18, 2012   (EP) .................................. 12197844

(51) Int. Cl.
*B32B 41/00*    (2006.01)
*A61C 13/00*    (2006.01)
(Continued)

(52) U.S. Cl.
CPC ...... *A61C 13/0004* (2013.01); *A61C 13/0019* (2013.01); *A61C 13/082* (2013.01);
(Continued)

(58) Field of Classification Search
CPC . A61C 13/0004; A61C 13/0019; A61C 13/20; A61C 13/082; A61C 13/09; F27B 17/025; F27D 19/00; F27D 2019/0028
(Continued)

(56) References Cited

U.S. PATENT DOCUMENTS 5,121,334 A * 6/1992 Riley ................. A61C 13/0004
345/419
2005/0175949 A1* 8/2005 Grunenfelder ......... A61C 13/20
432/120
(Continued)

FOREIGN PATENT DOCUMENTS

EP    1555499 A1    7/2005
EP    1561433 A1    8/2005
(Continued)

*Primary Examiner* — Michael N Orlando
*Assistant Examiner* — Joshel Rivera
(74) *Attorney, Agent, or Firm* — Ann M. Knab; Thad McMurray

(57) ABSTRACT

A process for manufacturing a dental restoration part as well as a dental furnace are provided in which the dental restoration part is produced on a foundation by means of applying at least two layers, wherein initial data, in particular three-dimensional data of the foundation, are stored in a memory device, and picture data, in particular three-dimensional data concerning the outer contour of the dental restoration part to be produced and the layers of the dental restoration part to be applied, are determined and in particular stored. It is provided that the dental restoration part is positioned at least partially during its production within the picture recording area of a picture recording device (30), and that before finishing the dental restoration part (20) and upon the application of at least one layer, the latter is recorded at least with regards to the thickness of the layer and/or its color, is displayed in particular via a display device (16). Furthermore, the layer recorded is compared with the picture data
(Continued)

Figure 1:
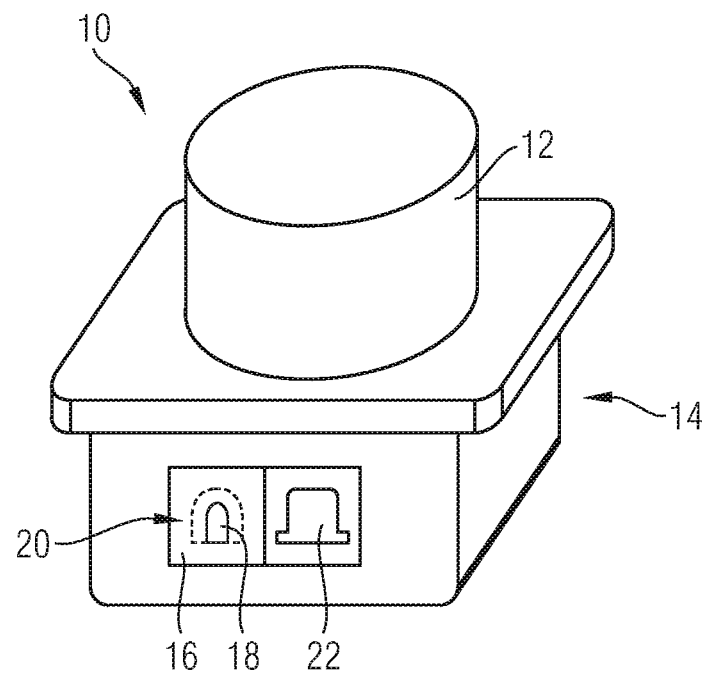

(32) at least regarding the thickness of the layer. An error signal is produced if the layer applied does not correspond to the predetermined layer in accordance with the picture data (32) regarding the thickness of the layer and/or the color and/or the other parameters.

21 Claims, 2 Drawing Sheets

(51) Int. Cl.
    *A61C 13/08*     (2006.01)
    *A61C 13/09*     (2006.01)
    *A61C 13/20*     (2006.01)
    *F27B 17/02*     (2006.01)
    *F27D 19/00*     (2006.01)

(52) U.S. Cl.
    CPC .............. *A61C 13/09* (2013.01); *A61C 13/20* (2013.01); *F27B 17/025* (2013.01); *F27D 19/00* (2013.01); *F27D 2019/0028* (2013.01)

(58) Field of Classification Search
    USPC ........................... 156/64, 350, 351, 378, 379
    See application file for complete search history.

(56) References Cited

U.S. PATENT DOCUMENTS

| | | | |
|---|---|---|---|
| 2009/0117504 A1* | 5/2009 | Grunenfelder | A61C 13/20 432/51 |
| 2013/0026157 A1 | 1/2013 | Jussel et al. | |
| 2013/0029280 A1 | 1/2013 | Jussel et al. | |

FOREIGN PATENT DOCUMENTS

| | | |
|---|---|---|
| EP | 2550928 A1 | 1/2013 |
| EP | 2551621 A1 | 1/2013 |
| WO | 00/08415 A1 | 2/2000 |

* cited by examiner

PROCESS FOR MANUFACTURING A DENTAL RESTORATION PART AND A DENTAL FURNACE FOR MANUFACTURING THE SAME

CROSS-REFERENCE TO RELATED APPLICATIONS

This application is a National Stage application of International patent application PCT/EP2013/072287 filed on Oct. 24, 2013, which claims priority to European patent application No. 12197844.9 filed on Dec. 18, 2012, the disclosures of which are incorporated herein by reference in their entirety.

The invention concerns a process for manufacturing a dental restoration part in accordance with the preamble of Claim 1, as well as a dental furnace in accordance with the preamble of Claim 15.

It has been known for longer that the quality of dental restoration parts produced depends on how the dental restoration part to be produced is harmonised with the neighbouring teeth. This holds true both with regards to shape and color, but also, for instance, color gradient and translucency.

In order to produce an appearance of the dental restoration part which is as lifelike and harmonic as possible, it has become known to record the neighbouring teeth with the help of a camera and produce the appearance of the dental restoration part depending on these.

With this, there is a disadvantage in that a 2D camera works only on a planar level, such that only the color variance of the neighbouring teeth can be reproduced in the dental restoration part, but not, for instance, the translucency.

Furthermore, it has become known to produce a dental restoration part with the help of CAD/CAM processes, based on the data acquired. One example for this can be taken from DE 101 13 753. It has also become known to quasi insert the tooth to be produced or the dental restoration part to be produced virtually into a depiction of the neighbouring teeth, in order to be able to better judge the impression of the dental restoration part to be produced. Such a process can be taken from German Patent 10 2004 002 724 B4.

All processes known have been suggested or published for a longer time already, but the result achieved depends largely on the experience and skill of the dental technician who is charged with the production of the dental restoration part.

In contrast to this, the invention is based on the task of providing a process for manufacturing a dental restoration part in accordance with the preamble of Claim 1 or, respectively, a dental furnace for the production of such a dental restoration part, in accordance with the preamble of Claim 15, which make possible an improved quality of the dental restoration parts produced.

This task is solved, in accordance with the present invention, by Claim 1. Advantageous embodiments result from the subordinate Claims.

In accordance with the present invention, a dental restoration part is produced in individual steps: The outer contour of the dental restoration part to be produced is determined by means of a three-dimensional recording of the neighbouring teeth, for instance with the help of 3D cameras. Furthermore, the foundation is determined—also in a three-dimensional fashion—, and is stored in a memory device. It is to be understood in this respect that the memory device can store a multitude of possible foundation data in advance, which are "suitable" for the dental restoration part to be produced, whereas the three-dimensional surface picture of the dental restoration part differs case-by-case.

Advantageously, a suitable foundation can now be selected based on the three-dimensional surface data which correspond to the outer contour of the dental restoration part to be produced.

Since the foundation is clearly spaced from the outer contour in all positions, its optical impression is lowest compared with the remaining dental restoration part.

In accordance with the present invention, the difference space, i.e. the three-dimensional structure between the foundation and the outer contour to be produced, is split up into layers which are to be applied.

The dental restoration part is now produced in such a fashion that it during the manufacture of the semi-finished product, i.e. the dental restoration part before its being finished, is visually recorded, which recording is done via a picture recording device. The picture recording device can then record at least one layer, and this layer is also displayed via a display device in an advantageous embodiment. In this process, it is at least the thickness of the layer and the color of the layer which are recorded in a virtually automated fashion via the picture recording device.

In accordance with the present invention, the layer recorded is now compared, at least with regards to its layer thickness, with the reference picture data, and an error signal is created if the layer applied does not correspond to the predetermined layer in accordance with the picture data with regards to the layer thickness and/or color and/or other parameters. The picture data consist insofar of three-dimensional data of the outer contour of the dental restoration part to be produced, as well as of three-dimensional transition data, i.e. data concerning the layer to be produced, based on the foundation and/or the difference between the foundation and the outer contour.

The error signal is created whenever the deviation between the predetermined layer data in accordance with the picture data and the values recorded by the picture recording device exceeds a threshold value. If the deviation is lower than the threshold value, the thickness of the layer or another parameter of the subsequent layer is simply adapted accordingly.

This is done, by way of example, in such a fashion that, if the thickness of the layer which has been applied to the foundation is 5% larger than has been predetermined at one position, the subsequent layer is adapted accordingly with regards to its layer thickness, i.e. is produced thinner to such a degree at this position as corresponds to the 5%.

Surprisingly, with the help of the control of layer thickness or control of layer parameters in accordance with the present invention, it is possible to considerably improve the structure of a dental restoration part, and in particular become more independent from the skill and experience of the dental technician charged. The dental technician will automatically be given hints during the production of the dental restoration part, for instance on a display device, that certain parameters are not quite correct in certain positions, and hints are presented automatically as to how the respective deviations are to be corrected in the layer to be applied next.

This holds true equally for color mistakes which can also be balanced and/or compensated for to a certain degree if appearing in the lower layers, which is done by then counteracting with regards to the color in the subsequent layer.

In an advantageous embodiment, a tracking device is provided which tracks the picture recording device in the recording of the dental restoration part during its production, such that the surface of the respective layer which is recorded three-dimensionally is always positioned in the focus of the picture recording device.

The display on the display device for depicting the layer applied can be done in any way and fashion, preferably both in the form of lines or envelope curves and as numeric values.

In another advantageous embodiment, data spectacles or a head-mounted display are provided as the display device, which will then immediately blend in with the picture recorded by the three-dimensional camera the corrections for the layers to be applied next or the layer to be applied next in the sense of mixed reality.

The process in accordance with the present invention can be applied both with ceramic or composite dental restoration parts and with dental restoration parts to be polymerised, and it is favourable that the process in accordance with the present invention can be put into practice iteratively, such that the same steps can be put into practice with the help of the same equipment from layer to layer until the last layer.

Both in the dental furnace and during polymerisation, the dental restoration material applied is typically subject to shrinking. This can preferably be compensated for, either by applying the current layer with a certain excess, or by allowing for some excess in the next layer, in order to compensate for shrinkage.

It is to be understood that the layers can be applied in such a fashion that a step of polymerisation follows the application of each layer, in particular if using materials to be polymerised, such that the result of shrinkage can be compensated for with the help of the picture recording device in accordance with the present invention.

In the realisation of the dental restoration part as a dental restoration part to be fired in a dental furnace, a programme control of the furnace based on the comparison result of the comparison between the picture recorded of the dental restoration part to be produced and the picture data can be carried out, which are stored in the dental furnace or separate from the latter in advance, in particular in a memory device which comprises a database, and a security function can be integrated which prevents the furnace from switching on if the divergence between the picture of the picture recording device recorded and the picture stored exceeds a predetermined level.

Here, the deviation can either be recorded automatically by means of image evaluation, or alternatively by means of visual assessment.

It is also possible to place the two pictures on top of each other electronically and highlight the differences by means of colouring the differences, in order to give the user hints as to the deviations and allow a corresponding judgement with regards to the further steps to be taken.

[The Advantages of the Subclaims Carry on From Here]

Figure 2:
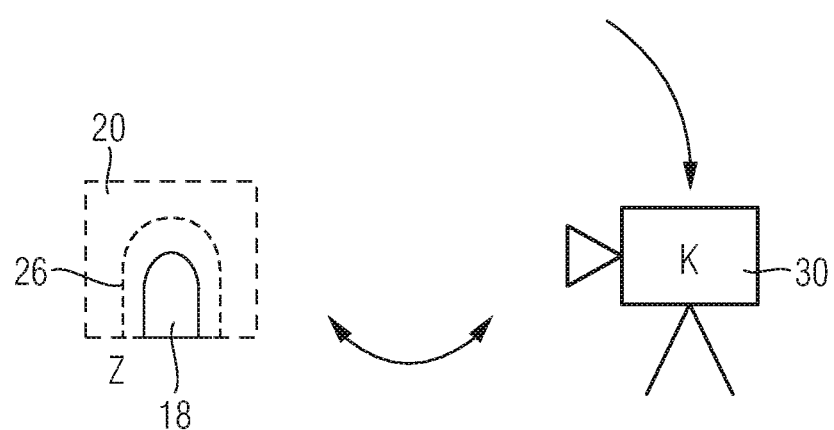
Figure 3:
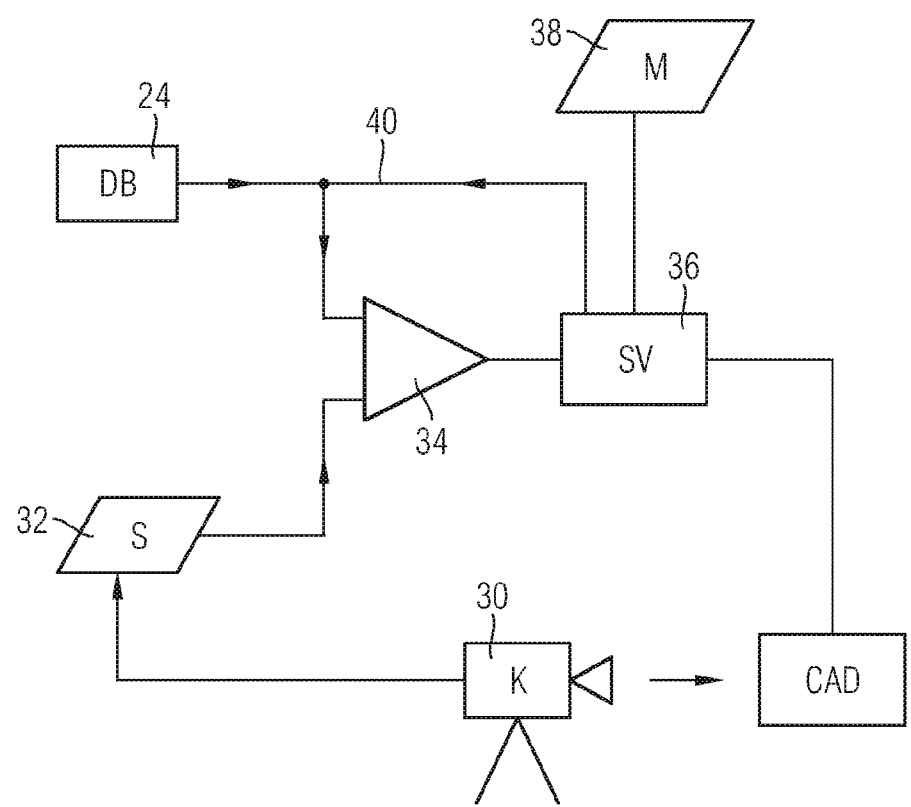

Further advantages, details and features result from the underneath description of one exemplary embodiment of the invention with reference to the Figures which show:

FIG. 1 a schematic view of a dental furnace in accordance with the present invention, for the exemplary description of a process in accordance with the present invention;

FIG. 2 a schematic depiction of a picture recording device in accordance with the present invention, with the partly produced dental restoration part; and FIG. 3 a schematically depicted function of the process in accordance with the present invention.

The dental furnace 10 depicted in FIG. 1 comprises, in the embodiment depicted, a furnace hood 12 and a furnace base 14 on which the furnace hood 12 is supported in a basically known fashion in such a way that it can be swivelled.

In the depiction in accordance with FIG. 1, furnace base 14 comprises a display device 16 at its front portion. Display device 16 is used in accordance with the present invention, wherein a foundation 18 of a dental restoration is depicted with solid lines in the left portion in the state of operation depicted, and a tooth to be applied to it as a dental restoration 20 with broken lines.

In contrast, a tooth 22 is depicted in the right portion of display device 16, whose picture has been acquired from a picture recording device, wherein the neighbouring teeth to tooth 20 to be produced are depicted.

This display basically presents to the dental technician the way in what layers in accordance with the present invention he needs to build up foundation 18 in order to end up with tooth 22.

Whereas the process in accordance with the present invention has been illustrated here with the help of a dental furnace, it is to be understood that the invention allows equally also the production of a dental restoration part with the help of a polymerisation device.

In FIG. 2, tooth Z 20 is depicted schematically, in this case with its outer contour in broken lines. Foundation 18 is again depicted with solid lines. In electronic form, both depictions are available in three-dimensional form, i.e. as an envelope curve in the space, wherein the data of the foundation are stored in a memory device 24 in the style of a database in order to facilitate the construction of the individual layers. In accordance with the present invention, a first layer, whose outlines 26 are depicted schematically in FIG. 1, is now applied to foundation 18.

This can be done in any suitable fashion, for instance also via one of the known rapid-prototyping processes, wherein the thickness of the layers will then result from the number and arrangement of the voxels applied.

The layer thickness of the layer of outline 26 is determined in advance in a suitable fashion, for instance by calculating the spatial difference between the foundation 18 and the outer contour 20 of the tooth. It is to be understood that it is preferable that each layer has essentially the same layer thickness, if only in order to be able to realise a uniform curing quickly during the process of polymerisation. If, for example, the application of three layers is necessary, in accordance with FIG. 2, in order to reach the desired layer thickness and thus the outer contour 20, the layer thickness of the first layer 26 is determined to be approximately one third of the entire thickness of layers.

The layer thickness achieved in fact and its three-dimensional outer contour are determined, in accordance with the present invention, with the help of a picture recording device 30 which is available in the form of a three-dimensional camera, or a camera which can be swivelled around all space axes and from which a three-dimensional picture can be obtained.

It can be taken from FIG. 3 that first based on a memory device 24 basic data are provided, for instance of foundation 18 or, for example, data of the surroundings into which the tooth is to be applied. At the same time, a picture 32 of camera 30 is displayed, which the latter has acquired from neighbouring teeth and which, for example, reflects the target outer contour of the dental restoration part to be produced, or a picture of tooth 22.

The respective picture data are evaluated electronically and are processed, such that a three-dimensional comparison is possible. For this purpose, in accordance with FIG. 3, a comparison device 34 is provided which can of course also be realised in electronic form via software and which basically carries out a target/actual comparison.

In the first step, a large difference results from the comparison between target and actual values.

With the help of control device 36, however, it is not the process step of virtually filling in this difference in one go which is predetermined. Rather, the control device creates a target picture on a monitor 38 for a first layer to be created, which is created by the control device based on a target/actual comparison and a corresponding division in one integer value, for instance 3, or 8 too.

Accordingly, in case of a number of layers amounting to 8, the target picture displayed on monitor 38 will differ only little from the actual picture of foundation 18 in the first step of the process, on which the camera is directed for the comparison of target and actual results.

The number of layers is freely selectable by the dental technician, wherein with regards to the material selected and the layer thicknesses to be achieved with this, specifications are provided by control device 36. If, for example, the material to be polymerised is specified to be suitable for a maximum layer thickness of 1 mm, and a molar is to be realised with a total thickness of layers of 4 mm, all values of 1 to 3 are blocked for input by the user, such that only a number of layers of 4 to, for instance, 10 can be set.

The setting and interaction with the user can herein be realised via display device 16, which is then provided as a touch screen, or also in a basically known fashion via separate user keys, for instance to the right and left sides of display device 16 in FIG. 1, or a corresponding display in case a polymerisation device is used.

After the thickness of layers and also the selection of material, color shade and color variance and also further chromatic parameters including transparency have been preset, the application of the desired layer will be done preferably via a CAD/CAM system as can be taken from FIG. 3, which is controlled by control device 36.

It is to be understood that it is also possible instead to apply the layer manually in accordance with the specification by the control device.

During the process of application, but latest when the application of the respective layer has been finished, picture recording device 30, as explained above as a three-dimensional picture recording device, is directed to the semi-finished product of the dental restoration part, such that the advance of the application is under control permanently, or at least at regularly repeating intervals.

In this next step, a comparison is then made in a target/actual comparison with the specification branched off from control device 36, for which purpose connection line 40 is depicted in FIG. 3.

The application of the next layer, its layer thickness, its color and similar parameters will then follow in the next step, again in control device 36. The latter has the target/actual comparison of comparison device 34 available, and control device 36 creates from this a deviation from the target of the originally intended layer construction then. If, for instance, it turns out that the previous layer is too thin by 5% at some position—for instance after polymerisation—, the subsequent layer will be created stronger by 5% at this position, such that a compensation is made insofar.

Besides the combination of thickness of layer and/or the faults induced there, however, a compensation of other parameters is made as well, as far as this is possible from a technical point of view. If, for instance, one layer has been realised with a material that is too transparent or too little dark compared with the construction of layers as planned originally, the next layer can be realised with a more opaque or darker material, respectively, without considerably changing the aesthetic overall impression. This holds true in particular for the lower layers.

In the same fashion as described here with reference to the first and second layers, the controlled construction of layers is then done for the further layers too. In accordance with the present invention, at least two layers are provided, but it is also possible to use a multitude of layers, such as ten layers, for instance.

Whereas the camera and monitor as well as display device 16 in accordance with FIG. 1 are depicted here as separate construction units, it is to be understood that either the monitor and the camera, or display device 16 and camera 30 can be combined together in a suitable fashion with what is referred to as multi-media spectacles, which blend in the picture to be displayed with the natural picture of the dental restoration in the style of a virtual reality.

It is to be understood that it is the basically known layers that can be realised as layers, but also sub-layers of the basically known layers. The basically known layers include the opaque layer, the dentinal layer and the enamel layer (dental enamel layer), which can be divided into sub-layers each or as a whole.

The invention claimed is:

1. Process for manufacturing a dental restoration part comprising
    producing the dental restoration part on a foundation by means of applying at least two layers,
    wherein initial data comprising three-dimensional data of the foundation, are stored in a memory device, and picture data comprising three-dimensional data concerning the outer contour of the dental restoration part to be produced and layers of the dental restoration part to be applied, are determined and stored,
    wherein the dental restoration part is positioned at least partially during its production within the picture recording area of a picture recording device, and before finishing the dental restoration part and upon the application of at least one layer, the at least one layer is recorded at least with regard to a thickness of the at least one layer and/or its color, is displayed via a display device,
    the at least one layer recorded is compared with the picture data at least regarding the thickness of the at least one layer,
    an error signal is produced if the at least one layer applied does not correspond to a predetermined layer in accordance with the picture data regarding thickness of the at least one layer and/or color and/or other parameters,
    wherein the display device blends in the thickness and/or the color and/or the other parameters of a next layer of further dental material to be applied that is desired in accordance with a lamination program with the picture recorded by the camera in a sense of a mixed reality
    wherein the step of comparing continues until the restoration is complete.

2. Process in accordance with claim 1, wherein the display device is manufactured as data spectacles or as a head-mounted display.

3. Process in accordance with claim 1, wherein when the next layer is applied, a deviation between the predetermined layer data stored in the memory device and layer data of a previously applied layer recorded is taken into account by means of adapting layer thickness and/or color of the next layer.

4. Process in accordance with claim 1, wherein after recording with help of the picture recording device the dental restoration part with at least one layer applied, a comparison with thicknesses of layers of the dental restoration part to be manufactured, which are stored in the memory device, is made via a comparison device, and wherein a display device displays the difference between a progression of a layer recorded relative to a contour of a semi-finished dental restoration part and the predetermined outer contour of the finished dental restoration part in accordance with the data of the memory device.

5. Process in accordance with claim 1, wherein a layer finished in a structure of layers is recorded with the help of the picture recording device concerning a color, and is compared to a desired color stored in the memory device, and wherein, if there is a difference in colors that exceeds a predetermined threshold value, the manufacturing of the dental restoration part is interrupted.

6. Process in accordance with claim 1, wherein the display device displays, in addition to the dental restoration part in a current state after application of a last layer, a contour of a first (26) and further layers, in accordance with the data stored in the memory device (24).

7. Process in accordance with claim 1, wherein a comparison is made with the help of a comparison device between thicknesses of layers stored in a memory device (24) and thicknesses of layers recorded.

8. Process in accordance with claim 7, wherein the comparison is made with the help of a comparison device between the thicknesses of layers stored in a memory device and the thicknesses of layers recorded at a multitude of monitored positions of a three-dimensional surface of the layer applied.

9. Process in accordance with claim 1, wherein the determination of the thickness of the layer applied is made at monitored positions by means of calculation of a difference, wherein the difference between a contour of the picture recorded after application of the layer and a contour of the picture before application of the layer is used as the basis of the calculation, and this is done at each of the positions monitored.

10. Process in accordance with claim 1, wherein the display device outputs the error signal when a difference between the thickness of the layer recorded and the thickness of the layer stored in the memory device in accordance with the lamination program is larger than a predetermined threshold value.

11. Process in accordance with claim 1, wherein the layer recorded by the picture recording device is divided into at least two sections extending three-dimensionally, each of the sections being compared with data stored in the memory device with the help of a comparison device.

12. Process in accordance with claim 1, wherein after the application of one layer, the layer is fired in a firing furnace together with the foundation or is polymerised with the help of a polymerisation device and wherein the further layers are applied iteratively in accordance with the same process.

13. Process in accordance with claim 1, wherein after recording the dental restoration part with at least one layer applied to it with the help of the picture recording device, a comparison is made via a comparison device with the thicknesses of the layers of the dental restoration part to be produced as stored in the memory device.

14. Process in accordance with claim 1, wherein after recording the dental restoration part with at least one layer applied to it with the help of the picture recording device, and after firing or polymerising this semi-finished dental restoration part (20), a comparison is made via a comparison device with the thicknesses of the layers of the dental restoration part to be produced as stored in the memory device.

15. Process in accordance with claim 13, wherein a display device displays the difference between a progression of the layer recorded corresponding to the contour of the semi-finished dental restoration part and the predetermined outer contour of the finished dental restoration part in accordance with the data of the memory device.

16. Process in accordance with claim 15, wherein a last layer which is required for provision of the dental restoration part is manufactured with an amount of excess which compensates for the shrinking during firing or polymerisation.

17. Process in accordance with claim 1, wherein the picture recording device includes a tracking device which keeps a relative position between the tracking device and the dental restoration part constant during the production of the dental restoration part in each recording of a picture by the picture recording device concerning distance, rotation angle and/or illumination.

18. Process in accordance with one claim 1, wherein the display device displays a progression of the layer applied in the form of lines or envelope curves via numeric values.

19. Dental furnace for firing and/or pressing dental restorations comprising a programmable control device by which the furnace
    carries out a firing cycle or a pressing cycle,
    an input device for the control device comprising a touch-activated screen, with a picture recording device which comprises a picture recording area that is positioned outside the furnace,
    wherein the control device comprises a memory device in which pictures and/or data of products for the dental restorations are stored in electronic form, and comprises a comparison device which compares a picture recorded with pictures stored and if there is a sufficient degree of correspondence, controls the furnace in accordance with a program suiting the product,
    wherein the stored pictures and/or data comprise three-dimensional data concerning an outer contour of a dental restoration part to be produced along with layers of the dental restoration part to be applied, and the recorded picture comprises the dental restoration part being produced having at least one layer of the dental restoration part, the at least one layer is recorded at least with regard to a thickness of the at least one layer and/or its color, and displayed via a display device,
    the at least one layer recorded is compared with the stored pictures and/or data at least regarding the thickness of the at least one layer,
    an error signal is produced if the at least one layer applied does not correspond to a predetermined layer in accordance with the picture data regarding thickness of the at least one layer and/or color and/or other parameters,
    wherein the display device blends in the thickness and/or the color and/or the other parameters of a next layer of further dental material to be applied that is desired in accordance with a lamination program with the picture recorded by the camera in a sense of a mixed reality,
    wherein the comparing of layers to pictures and/or data is continued until the restoration is complete.

20. Dental furnace in accordance with claim 19, wherein the comparison device presents the suitable program to the user on a display device of the dental furnace if there is a sufficient degree of correspondence, and wherein the program is started upon confirmation by the user.

21. Dental furnace in accordance with claim 19, wherein the memory comprises a database.

\* \* \* \* \*